US009847978B2

(12) United States Patent
Greenberg et al.

(10) Patent No.: US 9,847,978 B2
(45) Date of Patent: Dec. 19, 2017

(54) SECURE MOBILE AFFIRMATIVE CONSENT MANAGEMENT

(71) Applicant: Fast Dog, LLC, Boca Raton, FL (US)

(72) Inventors: Steven M. Greenberg, Boynton Beach, FL (US); Laurence Kahn, Montclair, NJ (US)

(73) Assignee: FAST DOG, LLC, Boca Raton, FL (US)

( * ) Notice: Subject to any disclaimer, the term of this patent is extended or adjusted under 35 U.S.C. 154(b) by 278 days.

(21) Appl. No.: 14/848,388

(22) Filed: Sep. 9, 2015

(65) Prior Publication Data

US 2017/0070487 A1 Mar. 9, 2017

(51) Int. Cl.
H04L 29/06 (2006.01)
G06F 19/00 (2011.01)

(52) U.S. Cl.
CPC ........ H04L 63/0442 (2013.01); H04L 63/061 (2013.01); H04L 63/0823 (2013.01); G06F 19/322 (2013.01); G06F 19/3418 (2013.01); G06F 19/3431 (2013.01)

(58) Field of Classification Search
CPC ............... H04L 63/0442; H04L 63/061; H04L 63/0823; G06F 19/322; G06F 19/3418; G06F 19/3431
See application file for complete search history.

(56) References Cited

U.S. PATENT DOCUMENTS

| 2003/0115154 | A1* | 6/2003 | Anderson | G06F 21/32 705/73 |
| 2014/0002798 | A1* | 1/2014 | Harris | A61B 5/4863 351/210 |
| 2014/0331282 | A1* | 11/2014 | Tkachev | H04L 63/08 726/3 |
| 2015/0213079 | A1* | 7/2015 | Shukla | G06F 17/30371 707/687 |

(Continued)

OTHER PUBLICATIONS

"Frequently Asked Questions—Good2Go App" Publication date of Sep. 26, 2014 verified by Internet Archive (54 pages total) http://web.archive.org/web/20140926072251/http://good2goapp.com/faq/.*

(Continued)

Primary Examiner — Joseph P Hirl
Assistant Examiner — Thomas Gyorfi
(74) Attorney, Agent, or Firm — Steven M. Greenberg, Esq.; CRGO Law

(57) ABSTRACT

A method, system and computer program product for secure mobile affirmative consent management is provided and includes receiving from a requesting individual a request to manage affirmative consent with a different individual. In response, the requesting individual is prompted to specify a self-assessed indication of sobriety and a sobriety test is administered to the requesting individual and a performance scored. The scored performance is compared with a pre-stored typical performance for individuals having a same self-assessed indication and the self-assessed indication is (Continued)

validated based upon the comparison. A payload is received from the different individual, and combined with data identifying the requesting individual, and including the validated self-assessed indication. Finally, the combination is stored in remote storage.

17 Claims, 5 Drawing Sheets

(56) References Cited

U.S. PATENT DOCUMENTS

| | | | |
|---|---|---|---|
| 2015/0269692 A1* | 9/2015 | Ryan | G06Q 50/18 705/311 |
| 2016/0086397 A1* | 3/2016 | Phillips | G07C 5/0808 701/32.4 |
| 2016/0314471 A1* | 10/2016 | Gerber | G06Q 20/4016 |

OTHER PUBLICATIONS

Amanda Hess. "Consensual Sex: There's an App for That" Article published Sep. 29, 2014 (4 pages) http://www.slate.com/blogs/xx_factor/2014/09/29/good2go_a_new_app_for_consenting_to_sex.html.*

Clark, Kelby, "App Aims to Put a New Face on Sexual Consent," Rutgers University, USA Today, Jul. 4, 2015.

Ramasastry, Anita, "Good2Go, Good and Gone, Why an Affirmative Consent App is a Risky Proposition," Verdict, JUSTIA, Oct. 21, 2014.

Timpf, Katherine, "Students Told to Take Photos With a 'Consent Contract' Before They Have Sex," National Review, Jul. 7, 2015.

Neff, Blake, "Sexual Consent Contracts Are Now a Real Thing You Can Buy," The Daily Caller, Jul. 8, 2015.

We Consent, isce.edu, Jul. 2015.

* cited by examiner

SECURE MOBILE AFFIRMATIVE CONSENT MANAGEMENT

BACKGROUND OF THE INVENTION

Field of the Invention

The present invention relates to electronic contracting and more particularly to affirmative consent contract management in a mobile device.

Description of the Related Art

Affirmative consent refers to the movement in which two individuals choose not to engage in intimate relations absent the affirmative consent to do so by each of the individuals. Previously, it had been customary for two individuals to choose not to engage in intimate relations upon one of the individuals affirmatively objecting to intimate relations. But, recent disputes at various academic institutions have called into question the wisdom of any individual engaging in an intimate act with another without first having received affirmative consent. To wit, in some governmental jurisdictions, affirmative consent is now statutory in so far as in some circumstances, the eligibility of an academic institution to receive governmental funding rests upon the institution adopting an affirmative consent policy for its students.

Affirmative consent, while intellectually a simple enough concept, in practice is substantially more challenging. In this regard, the fast pace at which an intimate relationship between two individuals arises oftentimes does not permit the opportunity for the individuals to pause and discuss the prospective intimate acts and to memorialize affirmative consent in a way so as to subsequently be reliable—particularly in a judicial, academic disciplinary, or law enforcement setting. Addressing the real world challenges to the contemporaneous memorialization of affirmative consent, a handful of mobile computing applications have been developed.

One such application relies upon the audio and video capture of both individuals providing consent to one another to engage in intimate relations. Once a face is detected, irrespective of the identity associated with the detected face, the video and audio are encrypted using local encryption on the mobile device and thereafter stored on the mobile device and eventually uploaded to a central repository wherein the encrypted video is encrypted again and stored for a multi-year period. However, in an era of constant data security lapses, maintaining a centralized repository of video of individuals agreeing to engage in intimate acts is only a mouse click away from mass publication. Further, prior to the uploading of the video imagery to the centralized repository, the possessor of the mobile device is free to publish the video to others without the consent of the other individual appearing in the video and consenting to engage in intimate relations.

Of note, it is apparent that merely consenting to intimate relations on camera is not sufficient for affirmative consent where the consenting individuals lack the capacity to consent. In this regard, it is widely understood that in the campus setting, consenting young adults may experience some degree of intoxication prior to seeking the affirmative consent of another individual for an intimate encounter. Legally, no person has the capacity to consent to intimate relations when that person is intoxicated. Thus, even if video imagery is acquired of an individual affirmatively consenting to an intimate encounter, if that individual is not sober, no consent will have been possible thereby defeating the intent of the consent mobile application.

Recognizing the inherent deficiency of consent applications lacking a confirmation of sobriety, a short-lived mobile application relied upon the manual specification of consent in a user interface of the application in the mobile device along with a self-assessment of sobriety. Were an individual seeking or providing affirmative consent to have indicated a degree of intoxication, no affirmative consent is permitted and the mobile application blocks subsequent attempts to record affirmative consent. Of course, the same data privacy concerns existed in this instance as before. More importantly, an intoxicated person is not a reliable judge of one's own degree of intoxication making the resultant recordation of affirmative consent highly unreliable. For both reasons, this particular mobile application survived only days of distribution before being retracted from the marketplace.

BRIEF SUMMARY OF THE INVENTION

Embodiments of the present invention address deficiencies of the art in respect to mobile management of affirmative consent and provide a novel and non-obvious method, system and computer program product for secure mobile affirmative consent management. In an embodiment of the invention, a secure mobile affirmative consent management method includes receiving from a requesting individual in a user interface to a mobile consent management application executing in memory of a mobile computing device, a request to manage affirmative consent with a different individual. In response, the requesting individual is prompted through the user interface to specify a self-assessed indication of sobriety. Thereafter, a sobriety test of the requesting individual is executed in the user interface and a performance of the requesting individual scored with respect to the sobriety test.

The scored performance is compared with a pre-stored typical performance for individuals having a same self-assessed indication of sobriety and the self-assessed indication of sobriety of the requesting individual is validated based upon the comparison. If the validation reflects a threshold level of sobriety, an asymmetrically encrypted payload is received in the device from the different individual, and is combined with data specifying an identity of the requesting individual, the validated self-assessed indication, and the self-assessed indication of sobriety. Finally, the combination is asymmetrically encrypted, and then further encrypting with an encryption key associated with remote storage to produce a triple encrypted package before being stored in the remote storage separate from a mobile device of either the requesting individual and the different individual.

In one aspect of the embodiment, the asymmetrically encrypted payload received from the different individual is asymmetrically encrypted using a public key of the different individual and is decryptable therefore using only a private key of the different individual. Further, the combination is asymmetrically encrypted using a public key of the requesting individual such that the asymmetrically encrypted combination is decryptable therefore using only a private key of the requesting individual. In yet another aspect of the embodiment, the encryption key associated with remote storage is a symmetric key retrieved in connection with the remote storage.

In a further aspect of the embodiment, the validating of the self-assessed indication of sobriety includes changing the self-assessed indication of sobriety to a different self-assessed indication of sobriety in response to a determination during the comparison that the scored performance differs from the pre-stored typical performance by a threshold amount. In this regard, the pre-stored typical performance for individuals having a same self-assessed indication of sobriety are pre-stored in a table disposed in persistent storage of the mobile computing device and updated on a periodic basis.

Finally, in even yet another aspect of the embodiment, a request to retrieve affirmative consent information pertaining to an event specified to have occurred in connection with a particular time of year is received in a server coupled to the fixed storage. In response, a set of all triple encrypted packages stored within a threshold period of time from the particular time of year is retrieved from the fixed storage and each of the triple encrypted packages decrypted using a decryption key associated with the remote storage. Thereafter, brute-force decryption is attempted upon the set using private keys for each of the requesting individual and the different individual. Consequently, two unencrypted sets of data resulting from the brute-force decryption are stored in memory of the server, in so far as the two unencrypted sets reflect the affirmative consent in response to the request.

In another embodiment of the invention, a mobile computing device is configured for secure mobile affirmative consent management. The device includes memory and at least one processor, and a display driven by the processor. The device also includes fixed storage storing data accessible by the processor and also a unique identifier of the mobile computing device. For instance, the unique identifier is a media access control (MAC) address of the mobile computing device. The device yet further includes an asymmetric key pair stored in the fixed storage. Finally, the device includes a secure mobile affirmative consent management module executing in the memory of the mobile computing device.

The module includes program code enabled during execution to receive from a requesting individual in a user interface to the mobile affirmative consent management module a request to manage affirmative consent with a different individual, and to respond to the request by prompting the requesting individual through the user interface to specify a self-assessed indication of sobriety, to execute a sobriety test of the requesting individual by one or more of the processors of the device in the user interface and to score a performance of the requesting individual for the sobriety test, to compare by the processor of the device the scored performance with a pre-stored typical performance for individuals having a same self-assessed indication of sobriety, to validate in the application the self-assessed indication of sobriety of the requesting individual based upon the comparison, and to respond to a validation of the self-assessed indication as reflecting a threshold level of sobriety by receiving in the device an asymmetrically encrypted payload from the different individual, combining in memory of the device the asymmetrically encrypted payload with data including the unique identifier, the validated self-assessed indication, and the self-assessed indication of sobriety, asymmetrically encrypting the combination, and uploading the asymmetrically encrypted combination to remote storage.

In one aspect of the embodiment, the asymmetrically encrypted combination is further encrypted by the program code prior to uploading with an encryption key associated with the remote storage in order to produce a triple encrypted package. In another aspect of the embodiment, the validation includes changing the self-assessed indication of sobriety to a different self-assessed indication of sobriety in response to a determination during the comparison that the scored performance differs from the pre-stored typical performance by a threshold amount. In yet another aspect of the embodiment, a quick response (QR) code scanner executes in the memory of the device, such that the asymmetrically encrypted payload is encoded in a quick response (QR) code scanned by the device and decoded with the QR code scanner.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for secure mobile affirmative consent management. In accordance with an embodiment of the invention, within a mobile affirmative consent application, in response to a request to memorialize affirmative consent amongst two different individuals, a self-assessed degree of sobriety is received for each of the individuals through respectively different user interfaces to the application in respectively different mobile computing devices. Thereafter, a brief sobriety test is administered to each of the individuals through the different user interfaces and a performance score for the tests recorded by the respectively different mobile devices.

The self-assessed degree of sobriety for each of the individuals is then validated as an actual degree of sobriety, or changed as necessary to an actual degree of sobriety, based upon a corresponding one of the performance scores and a typical performance score for others of the same self-assessed degree of sobriety. To the extent that the individuals are considered to lack a requisite degree of sobriety, no affirmative consent is recorded. However, if a requisite degree of sobriety is determined to exist with respect to both individuals, for each of the individuals, a corresponding identity, actual degree of sobriety, self-assessed degree of sobriety, performance score are packaged into an affirmative consent payload, asymmetrically encrypted and transmitted to the mobile device of the other individual.

Each individual receiving the encrypted payload of the other combines the packaged affirmative consent payload with the asymmetrically encrypted payload and asymmetrically encrypts the combination. Finally, for each of the individuals, the encrypted combination is again queued for uploading over a network to a centralized repository and the encrypted combination is again encrypted using an encryption key of the centralized repository. As such, the again encrypted combination is stored as a triple-encrypted package in connection with a time and date of receipt.

Subsequently, when proof of affirmative consent for an intimate encounter occurring on a particular date is desired, a set of all triple-encrypted packages received within a threshold period of time of the particular date are retrieved and initially decrypted using the encryption key for the centralized repository. Thereafter, brute-force decryption is attempted on the decrypted packages using the decryption keys of both individuals so that only the encrypted combinations having been asymmetrically encrypted in connection with the decryption keys will decrypt. In this way, the triple-encrypted packages are both stored and retrieved without regard to the identity of the individuals and are able to be retrieved only with three separately held decryption keys so that guaranteed data security remains present throughout the process.

Figure 1:
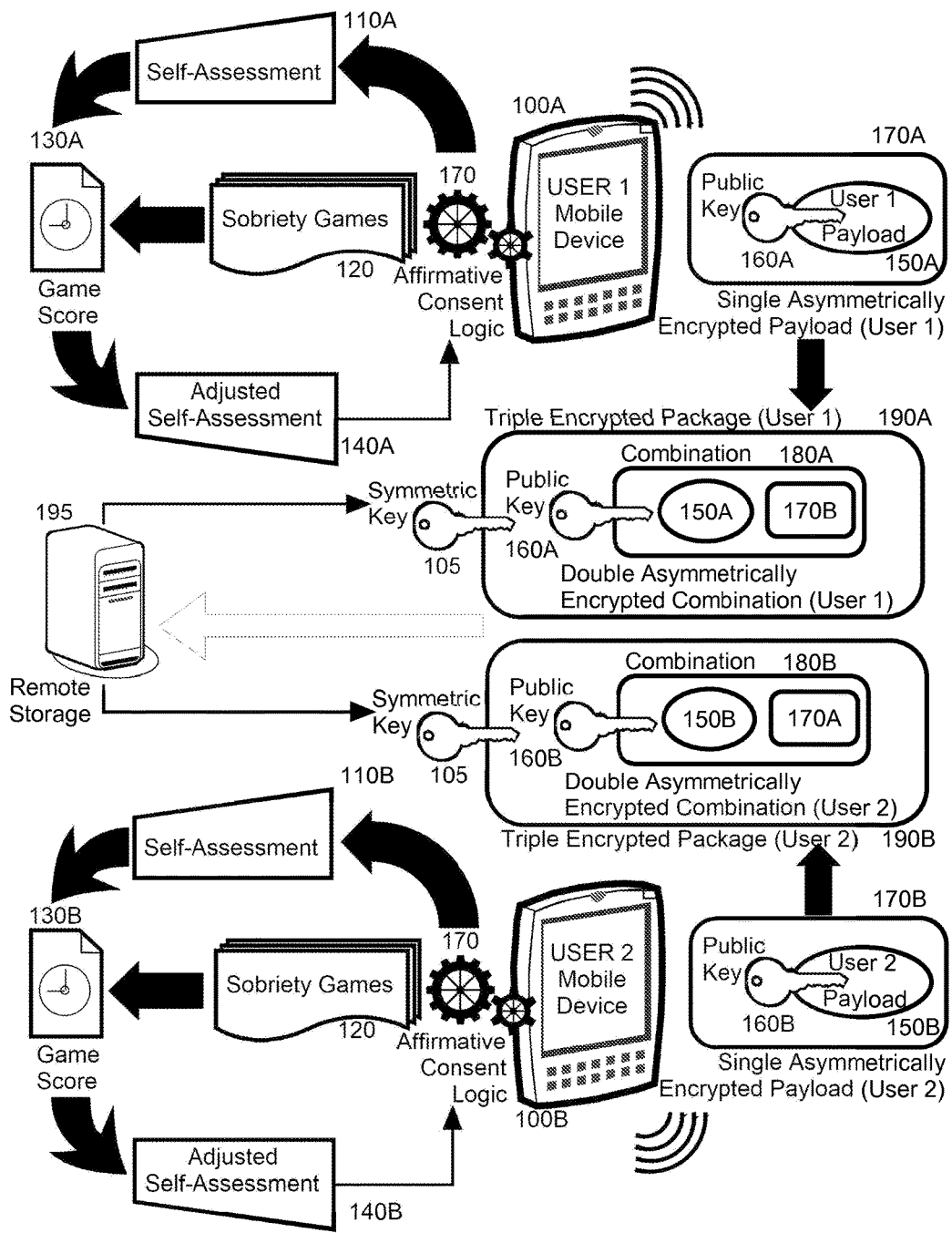
FIG. 1 is a pictorial illustration of a process for secure mobile affirmative consent management.

In further illustration, FIG. 1 pictorially shows a process for secure mobile affirmative consent management. As shown in FIG. 1, a pair of individuals can seek affirmative consent from one another through the use of respectively different mobile devices 100A, 100B in which respectively different instances of affirmative consent logic 170 executes. In response to a request by each end user, the affirmative consent logic 170 can prompt each respective end user to provide a self-assessment 110A, 110B of a mental and physical capacity to affirmatively consent. As a component of capacity, sobriety is a natural consideration. Consequently, the affirmative consent logic 170 presents to each one of the end users, one of a selection of different sobriety games 120. In this regard, the sobriety games each are time limited, dexterity tests presented in a corresponding display of the mobile devices 100A, 100B in which the reaction time and reaction accuracy of an end user are measured as a game score 130A, 130B in connection with a series of automated prompts. Examples include presenting a series of icons on a display at different random positions and measuring how quickly and how accurately an end user can touch the position of each of the presented icons. Other examples include how quickly and how accurately an end user can type an answer to a simplistic question, or how quickly and how accurately an end user can spell a presented word backwards.

Of note, once a game score 130A, 130B is computed for each of the end users in response to each of the end users completing a presented one of the sobriety games 120, the game score 130A, 130B of each of the end users is compared to a typical game score for other end users having a comparable self-assessment. The comparison is used to determine whether or not the self-assessment 110A, 110B of each end user is accurate. For instance, if a game score 130A, 130B of an end user with a corresponding self-assessment 110A, 110B deviates from an average game score for all other end users also specifying an equivalent game score by more than a threshold value, the self-assessment 110A, 110B of the corresponding one of the end users is modified into an adjusted self-assessment 140A, 140B associated with an average game score of other end users closer to equivalency to the actual game score 130A, 130B of the corresponding one of the end users.

Once an adjusted self-assessment 140A, 140B is computed for each of the end users in each of the mobile devices 100A, 110B by affirmative consent logic 170, the affirmative consent logic 170 combines for each end user, identifying information such as a MAC address of a corresponding one of the mobile devices 100A, 100B, the game score 130A, 130B, self-assessment 110A, 110B and adjusted self-assessment 140A into a payload 150A, 150B which is then encrypted using a corresponding public key 160A, 160B of the end user so as to produce a single asymmetrically encrypted payload 170A, 170B. The single asymmetrically encrypted payload 170A, 170B of each end user is then exchanged between the mobile devices 100A, 100B, for instance through wireless data communications such as short range radio frequency communications, or by optically scanning respective bar codes of the other, each of the bar codes encoding a corresponding one of the single asymmetrically encrypted payloads 170A, 170B.

Once the single asymmetrically encrypted payload 170A, 170B of the other of the end users is received by affirmative consent logic 170 of a corresponding one of the end users, the received one of the single asymmetrically encrypted payloads 170A, 170B is combined with the previously generated payload 150A, 150B and encrypted again using a corresponding public key 160A, 160B of the end user so as to produce a doubly asymmetrically encrypted combination 180A, 180B. Thereafter, each of the doubly asymmetrically encrypted combinations 180A, 180B are encrypted once again using a symmetric key 105 provided by remote storage 195 so as to produce a triple encrypted package 190A, 190B. Finally, each of the triple encrypted packages 190A, 190B are uploaded from a respective one of the mobile devices 100A, 100B to remote storage 195. Consequently, the game score 130A, 130B, self-assessment 110A, 110B and adjusted self-assessment 140A, 140B for each of the end users, representative of the affirmative consent of each of the end users, can be retrieved only with the possession of a private key of each end user for a corresponding one of the public keys 160A, 160B as well as the symmetric key 105.

Figure 2:
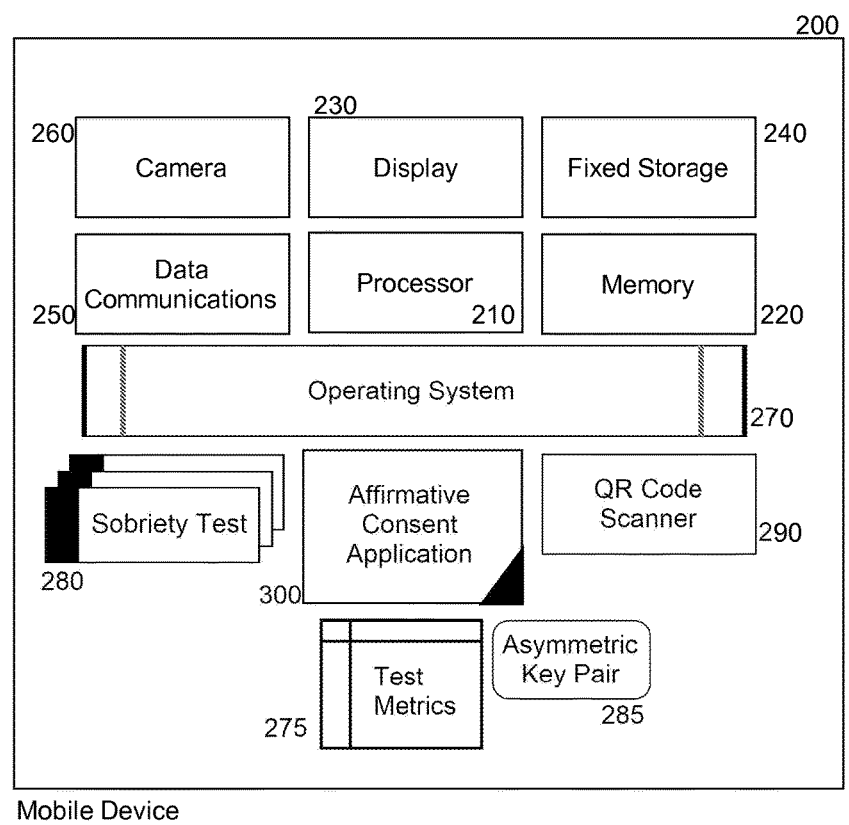
FIG. 2 is a schematic illustration of a mobile computing data processing system configured for secure mobile affirmative consent management.

The process described in connection with FIG. 1 is implemented in a mobile computing data processing system. In further illustration, FIG. 2 schematically shows a mobile computing data processing system configured for secure mobile affirmative consent management. The system includes a mobile device 200. The mobile device 200 is defined by a processor 210, memory 220, a display 230 and fixed storage 240 such as solid state memory or a fixed disk drive. Data communications circuitry 250 also is provided as is a digital camera 260. The foregoing is a common arrangement of components of a mobile computing device, as will be recognized by one of skill in the art, so as to permit the execution of an operating system 270 in the memory 220 by the processor 210 of the mobile device 200.

An affirmative consent module 300 is hosted within the operating system 270. The affirmative consent module 300 includes program code that when executes in the memory 220 by the processor 210, is enabled to respond to a request for affirmative consent by prompting in the display 230 for a self-assessment of sobriety, by presenting in the display 230 one of a selection of sobriety tests 280, by computing a score for the selected one of the sobriety tests 280, by comparing the computed score to test metrics 275 disposed in fixed storage 240, by adjusting the self-assessment according to the comparison, by generating a payload of the adjusted self-assessment and game score along with a MAC address of the mobile device 200, by encrypting the payload using a public key within an asymmetric key pair 285 disposed in fixed storage 240, by encoding the encrypted payload into a QR code and displaying the QR code in the display 230, by photographing a QR code displayed on a display of a different mobile device, by decoding the QR code using QR code scanner 290 and combining the decrypted QR code with the payload and encrypting the combination with the public key, by encrypting again the encrypted combination with a symmetric key in memory 220 to produce a triple encrypted package, and by transmitting the triple encrypted package to remote storage.

Figure 3:
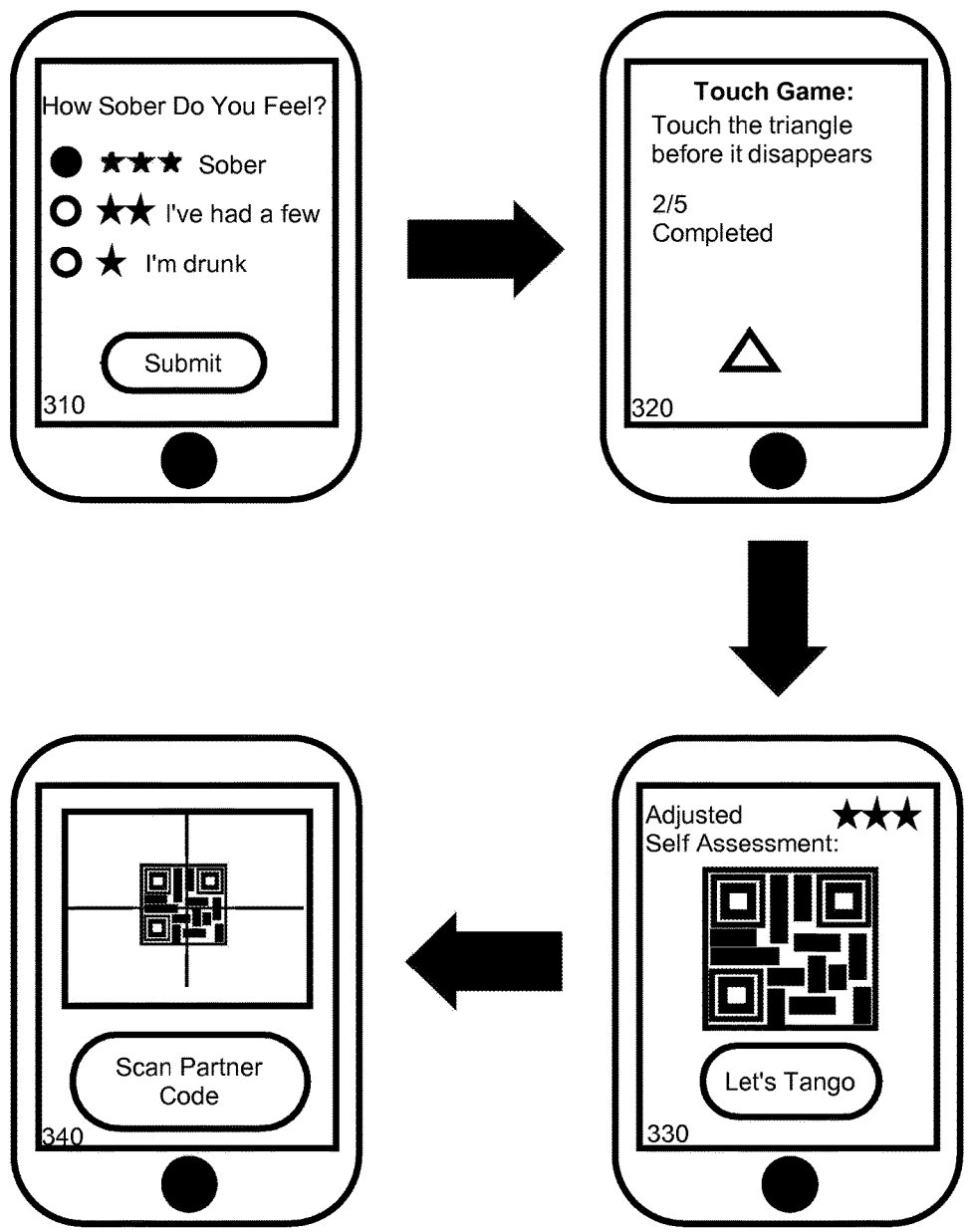
FIG. 3 is a pictorial illustration of a sequence of screen shots presented during secure mobile affirmative consent acquisition.

Of note, the affirmative consent logic 300 is configured to present a number of display screens in the display 230 in the course of secure mobile affirmative consent acquisition. In yet further illustration, FIG. 3 pictorially shows a sequence of screen shots presented in a mobile device to an end user during secure mobile affirmative consent acquisition. As shown in FIG. 3, the end user is prompted in a first screen 310 to provide a self-assessment. A number of different levels of sobriety can be suggested as part of the self-assessment though only three are shown in FIG. 3 for the purpose of illustrative simplicity. Thereafter, one of a selection of different sobriety games are presented in screen 320 and a score is computed for the end user based upon a performance of the end user in the sobriety game.

Optionally, based upon the computed score, the self-assessment is adjusted and a payload generated including identity data, the self-assessment and the game score, the payload then being encrypted. In screen 330, a QR code is generated that encodes the encrypted payload and the QR code is displayed for scanning for a different end user using a different mobile device. Likewise, in screen 340, the QR code of the different end user is scanned from the different device and decoded so as to supply an asymmetrically encrypted payload of the different end user. Thereafter, the payload of the end user is combined with the encrypted payload of the different end user and encrypted twice more before being transmitted to remote storage.

Figure 4A:
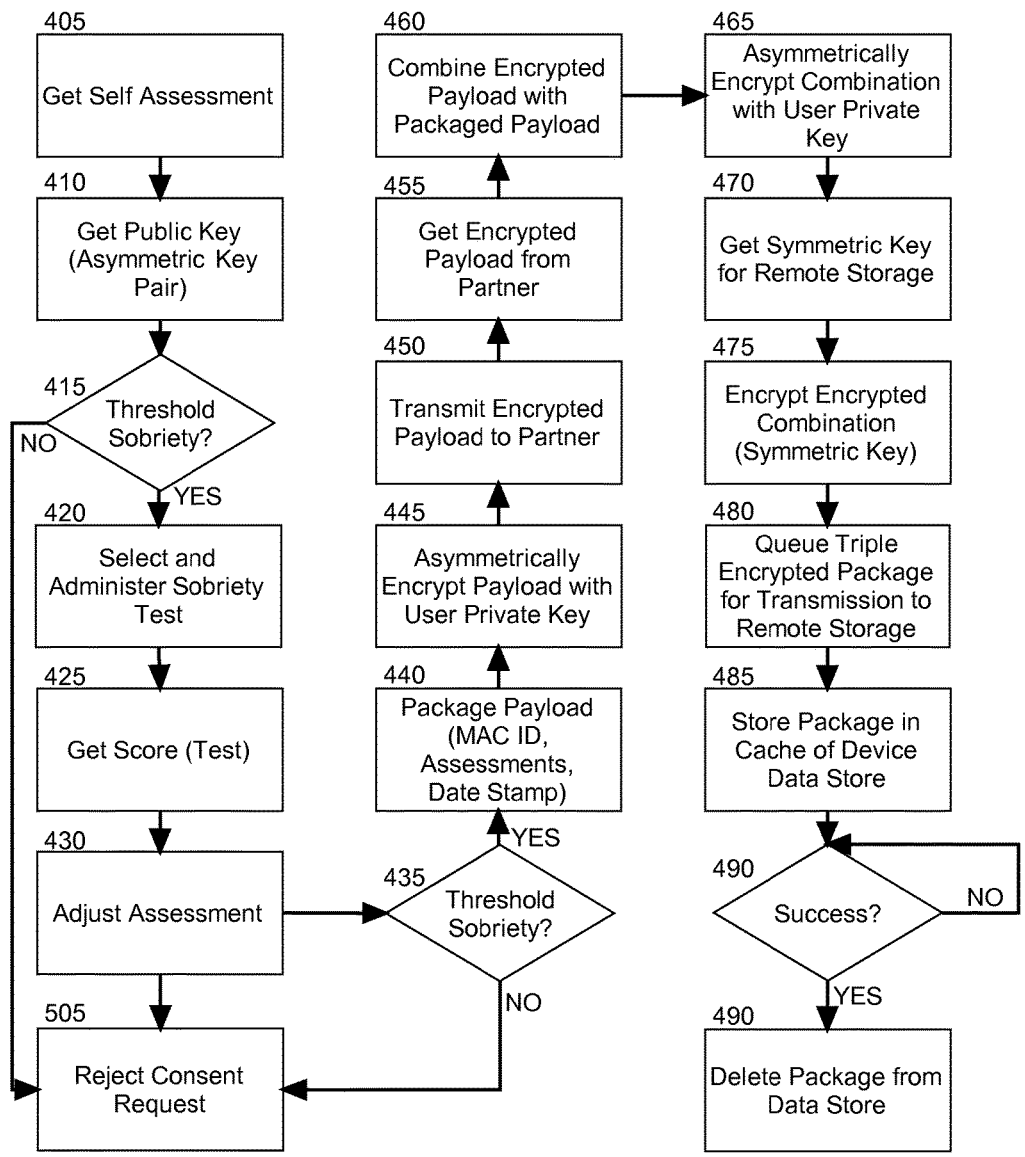
FIG. 4A is a flow chart illustrating a process for acquiring secure mobile affirmative consent; and, FIG. 4B is a flow chart illustrating a process for retrieving secure mobile affirmative consent.

In even yet further illustration of the operation of the affirmative consent module 300 of FIG. 2, FIG. 4A is a flow chart illustrating a process for acquiring secure mobile affirmative consent in an affirmative consent application executing in the memory of a mobile device. Beginning in block 405, in response to a request to document affirmative consent, a self-assessment is received for the end user and in block 410 a public key for the end user is loaded into memory. In decision block 415, it is determined whether or not the self-assessment presents a threshold degree of sobriety requisite to provide affirmative consent. If not, in block 505 the request is rejected. Otherwise, the process continues in block 420.

In block 420, a sobriety test is selected from amongst a selection of sobriety tests and administered to the end user. In block 430, a score is computed for the end user performing the sobriety test. As but one example, a time required for an end user to respond to a prompt in the sobriety test is measured and weighted based upon an accuracy of the response. For instance, to the extent that the sobriety test is a test in which a different sequence of icons are displayed on the screen of the mobile device in random positions and the end user is instructed to touch the icon once presented, a time required to touch the screen is measured as well as a distance from the position of the icon. The time and distance are combined into a single value, for instance by multiplication, and summed with other combinations for other icon presentations to produce a composite score. A lower value indicates a higher degree of performance with the end user touching the display in response to the presentation of an icon on the display more quickly and with greater accuracy.

The single value along with the self-assessment and game identifier is transmitted to a remote server that captures the combination of data without identifying information of the end user for use in computing an average score with other values produced by other end users to whom the game had been administered and from whom a common self-assessment had been established. Ultimately, a table of average scores for each game and each self-assessment is produced for all end users. The average score for each game and self-assessment value then is stored in each mobile device of each end user in the form of a table of average scores and standard deviations for each value of self-assessment and updated by the remote server periodically on each mobile device.

Consequently, in block 430, the computed score is then compared to the average score for the other end users of a same self-assessment who had previously been administered the same sobriety test. If the computed score differs from the average score by more than a threshold amount, for instance by more than one or two standard deviations away from the average score, the self-assessment is adjusted to a new self-assessment value that has an average score closer in value to the computed score. Subsequently, in decision block 435 it is determined whether or not the adjusted self-assessment still presents a threshold degree of sobriety requisite to provide affirmative consent. If not, in block 505 the request is rejected. Otherwise, the process continues in block 440. Optionally, even if in block 435 the adjusted self-assessment does not present a threshold degree of sobriety requisite to provide affirmative consent, the process may continue to block 440 so as to record the attempt for affirmative consent nonetheless.

In block 440, a payload is packaged to include a MAC identifier for the mobile device, the self-assessment (original or adjusted or both), and a time and/or date stamp to indicate when the affirmative consent had been recorded. In block 445, the payload is then asymmetrically encrypted using the public key in memory and in block 450 the asymmetrically encrypted payload is transmitted to a different mobile device of a different end user participating in the recordation of the affirmative consent. Likewise, in block 455 an encrypted payload is received in the mobile device from the different end user and in block 460 the received encrypted payload is combined with the packaged payload and encrypted using the public key in block 465. Finally, in block 470 a symmetric key for remote storage is retrieved from memory and used in block 475 to encrypt the encrypted combination to produce a triple encrypted package.

In block 480, the triple encrypted package is queued for transmission to remote storage, either by way of e-mail, text message, file transfer protocol (FTP) or direct communications with the remote storage. In block 485, the triple encrypted package is also stored in a cache in the mobile device that is separate from the affirmative consent application. In decision block 490, it is determined whether or not the triple encrypted package has been successfully transmitted. If so, the triple encrypted package is deleted from the cache in block 495. Of note, at startup, and periodically thereafter, the cache is inspected to determine if any triple encrypted packages are present. If so, those packages that are present are transmitted. In this way, even if the affirmative consent application is deleted from the mobile device before a triple encrypted package is able to be transmitted to remote storage, upon re-installation of the affirmative consent application, any triple encrypted packages remaining in the cache are transmitted to remote storage.

Figure 4B:
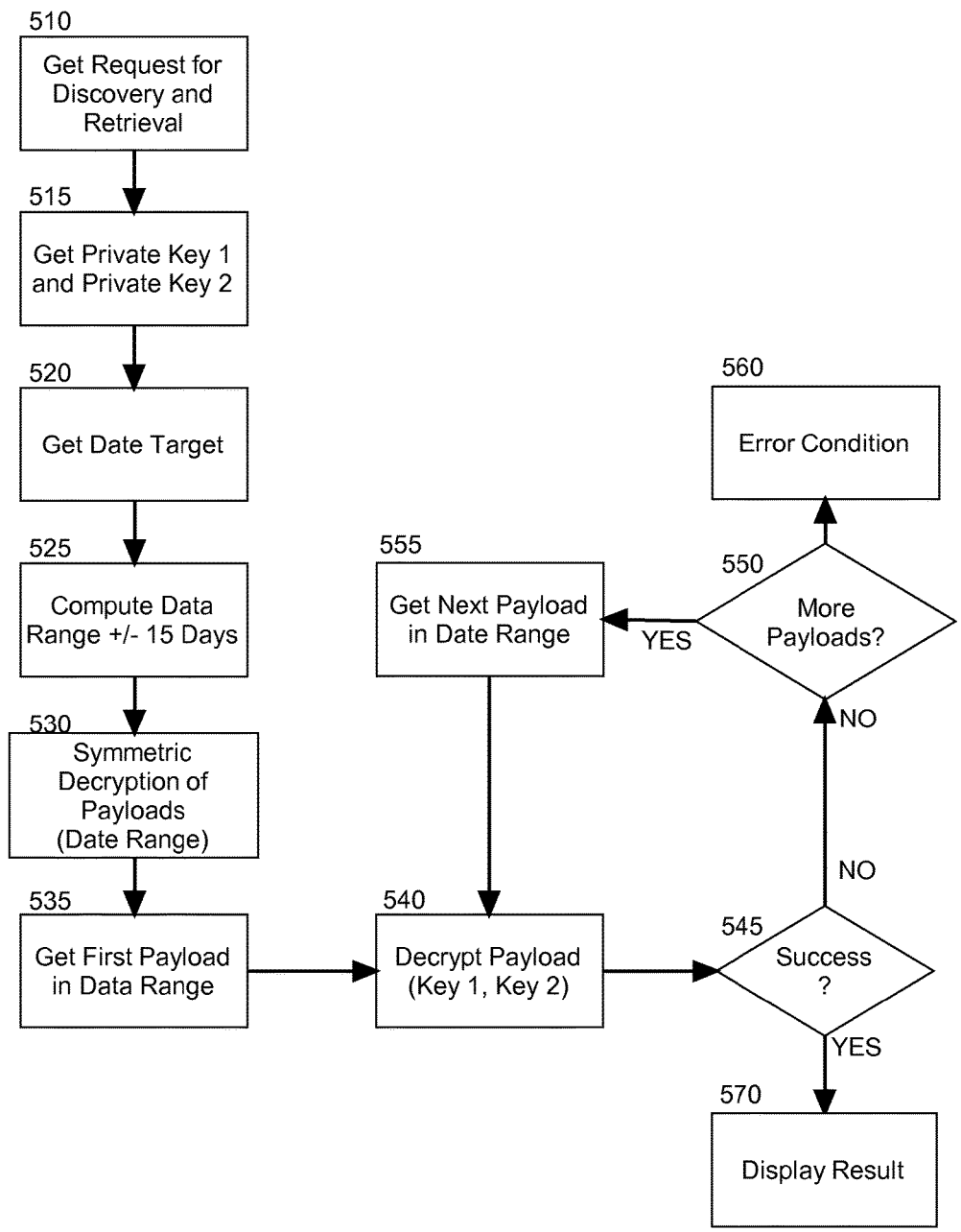

Once it is required to retrieve affirmative consent for two different end users, the affirmative consent can be retrieved through the use of private keys for each of the end users and a symmetric key of the remote storage. In even yet further illustration, FIG. 4B is a flow chart illustrating a process for retrieving secure mobile affirmative consent. Beginning in block 510, a request for discovery and retrieval of affirmative consent is received in a computer coupled to the remote storage. In block 515, the private key of each end user is received in memory and in block 520 a date target is provided in memory for when respectively different triple encrypted packages had been received from the end users. As such, in block 525 a date range is then computed based upon the target date.

In block 530, all triple encrypted payloads present in remote storage that had been received within the date range are retrieved in memory and decrypted using the symmetric key of the remote storage and in block 535 to produce a set of doubly encrypted payloads, a first one of the doubly encrypted payloads is loaded for processing. In block 540, a brute force attempt at decrypting the first doubly encrypted payload with each of the private keys is performed. The brute force attempt includes, as an example, utilizing each of the private keys so as to see if either is able to decrypt the first double encrypted payload so as to reveal data pertaining to a MAC identifier for a mobile device, a self-assessment (original or adjusted or both), a time and/or date stamp to indicate when the affirmative consent had been recorded and a singly encrypted payload to which the other of the private keys so as to reveal the remaining affirmative consent data. In decision block 545, if the brute force attempt is unsuccessful, if it is determined in decision block 550 that more doubly encrypted payloads remain to be processed, in block 555 a next one of the doubly encrypted payloads is loaded for processing and the brute force decryption is attempted again in block 540. In decision block 550, if no more doubly encrypted payloads remain to be brute force decrypted, the process ends in block 560 with an error condition. Otherwise, both now fully decrypted payloads are displayed as representative of the affirmative consent of both end users without having to have stored the affirmative consent of both end users in connection with any identifying information for either end user and while ensuring that no one end user can reveal the affirmative consent of the other without the cooperation of the other end user.

The present invention may be embodied within a system, a method, a computer program product or any combination thereof. The computer program product may include a computer readable storage medium or media having computer readable program instructions thereon for causing a processor to carry out aspects of the present invention. The computer readable storage medium is a tangible device that excludes transitory media, and can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language, and conventional procedural programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A secure mobile affirmative consent management method comprising:

receiving from a requesting individual in a user interface to a mobile consent management application executing in memory of a mobile computing device, a request to manage affirmative consent with a different individual, and responding to the request by prompting the requesting individual through the user interface to specify a self-assessed indication of sobriety;

executing a sobriety test of the requesting individual by a processor of the device in the user interface and scoring a performance of the requesting individual for the sobriety test;

comparing by the processor of the device the scored performance with a pre-stored typical performance for individuals having a same self-assessed indication of sobriety;

validating in the application the self-assessed indication of sobriety of the requesting individual based upon the comparison; and, responsive to a validation of the self-assessed indication as reflecting a threshold level of sobriety, receiving in the device a payload from the different individual, combining in a package in memory of the device, the payload with data specifying an identity of the requesting individual and the validated self-assessed indication, and storing the package in remote storage separate from a mobile device of either the requesting individual and the different individual, wherein the payload received from the different individual is asymmetrically encrypted with a public key of an asymmetric key pair of the different individual so as to be decryptable using a corresponding private key of the asymmetric key pair of the different individual, wherein the package is asymmetrically encrypted with a public key of an asymmetric key pair stored in the memory of the mobile computing device so as to be decryptable using a corresponding private key of the asymmetric key pair stored in the memory of the mobile computing device, and wherein the asymmetrically encrypted combination is encrypted with an encryption key associated with the remote storage to produce a triple encrypted package.

2. The method of claim 1, wherein the validating of the self-assessed indication of sobriety comprises changing the self-assessed indication of sobriety to a different self-assessed indication of sobriety in response to a determination during the comparison that the scored performance differs from the pre-stored typical performance by a threshold amount.

3. The method of claim 1, wherein the encryption key associated with remote storage is a symmetric key retrieved in connection with the remote storage.

4. The method of claim 1, wherein the pre-stored typical performance for individuals having a same self-assessed indication of sobriety are pre-stored in a table disposed in persistent storage of the mobile computing device and updated on a periodic basis.

5. The method of claim 1, further comprising:
receiving in a server coupled to the fixed storage a request to retrieve affirmative consent information pertaining to an event specified to have occurred in connection with a particular time of year;
retrieving from the fixed storage a set of all triple encrypted packages stored within a threshold period of time from the particular time of year;
decrypting each of the triple encrypted packages using a decryption key associated with the remote storage; attempting brute-force decryption to the set using private keys for each of the requesting individual and the different individual; and,
storing in memory of the server two unencrypted sets of data resulting from the brute-force decryption, the two unencrypted sets reflecting the affirmative consent in response to the request.

6. A mobile computing device configured for secure mobile affirmative consent management, the device comprising:
memory and at least one processor, and a display driven by the processor;
fixed storage storing data accessible by the processor and also a unique identifier of the mobile computing device; and,
a secure mobile affirmative consent management module executing in the memory of the mobile computing device, the module comprising program code enabled during execution to receive from a requesting individual in a user interface to the mobile affirmative consent management module a request to manage affirmative consent with a different individual, and to respond to the request by prompting the requesting individual through the user interface to specify a self-assessed indication of sobriety, to execute a sobriety test of the requesting individual by one or more of the processors of the device in the user interface and to score a performance of the requesting individual for the sobriety test, to compare by the processor of the device the scored performance with a pre-stored typical performance for individuals having a same self-assessed indication of sobriety, to validate in the application the self-assessed indication of sobriety of the requesting individual based upon the comparison, and to respond to a validation of the self-assessed indication as reflecting a threshold level of sobriety by receiving in the device a payload from the different individual, combining into a package in memory of the device the payload with data including the unique identifier and the validated self-assessed indication and uploading the package to remote storage,
wherein the payload received from the different individual is asymmetrically encrypted with a public key of an asymmetric key pair of the different individual so as to be decryptable using a corresponding private key of the asymmetric key pair of the different individual, wherein the package is asymmetrically encrypted with a public key of an asymmetric key pair stored in the memory of the mobile computing device so as to be decryptable using a corresponding private key of the asymmetric key pair stored in the memory of the mobile computing device, and wherein the asymmetrically encrypted combination is encrypted with an encryption key associated with the remote storage to produce a triple encrypted package.

7. The system of claim 6, wherein the package is further encrypted by the program code prior to uploading with the encryption key in order to produce the triple encrypted package.

8. The system of claim 6, wherein the unique identifier is a media access control (MAC) address of the mobile computing device.

9. The system of claim 6, wherein the validation comprises changing the self-assessed indication of sobriety to a different self-assessed indication of sobriety in response to a determination during the comparison that the scored performance differs from the pre-stored typical performance by a threshold amount.

10. The system of claim 6, further comprising a quick response (QR) code scanner executing in the memory of the device, wherein the asymmetrically encrypted payload is encoded in a quick response (QR) code scanned by the device and decoded with the QR code scanner.

11. The system of claim 6, wherein the encryption key associated with remote storage is a symmetric key retrieved in connection with the remote storage.

12. The system of claim 6, wherein the pre-stored typical performance for individuals having a same self-assessed indication of sobriety are pre-stored in a table in fixed storage and updated from over a computer communications network on a periodic basis.

13. A computer program product for secure mobile affirmative consent management, the computer program product comprising a non-transitory computer readable storage medium having program instructions embodied therewith, the program instructions executable by a device to cause the device to perform a method comprising:
receiving from a requesting individual in a user interface to a mobile consent management application executing in memory of a mobile computing device, a request to manage affirmative consent with a different individual, and responding to the request by prompting the requesting individual through the user interface to specify a self-assessed indication of sobriety;
executing a sobriety test of the requesting individual by a processor of the device in the user interface and scoring a performance of the requesting individual for the sobriety test;
comparing by the processor of the device the scored performance with a pre-stored typical performance for individuals having a same self-assessed indication of sobriety;
validating in the application the self-assessed indication of sobriety of the requesting individual based upon the comparison; and, responsive to a validation of the self-assessed indication as reflecting a threshold level of sobriety, receiving in the device a payload from the different individual, combining in a package in memory of the device, the payload with data specifying an identity of the requesting individual and the validated self-assessed indication, and storing the package in remote storage separate from a mobile device of either the requesting individual and the different individual,
wherein the payload received from the different individual is asymmetrically encrypted with a public key of an asymmetric key pair of the different individual so as to be decryptable using a corresponding private key of the asymmetric key pair of the different individual, wherein the package is asymmetrically encrypted with a public key of an asymmetric key pair stored in the memory of the mobile computing device so as to be decryptable using a corresponding private key of the asymmetric key pair stored in the memory of the mobile computing device, and wherein the asymmetrically encrypted combination is encrypted with an encryption key associated with the remote storage to produce a triple encrypted package.

14. The computer program product of claim 13, wherein the validating of the self-assessed indication of sobriety comprises changing the self-assessed indication of sobriety to a different self-assessed indication of sobriety in response to a determination during the comparison that the scored performance differs from the pre-stored typical performance by a threshold amount.

15. The computer program product of claim 13, wherein the encryption key associated with remote storage is a symmetric key retrieved in connection with the remote storage.

16. The computer program product of claim 13, wherein the pre-stored typical performance for individuals having a same self-assessed indication of sobriety are pre-stored in a table disposed in persistent storage of the mobile computing device and updated on a periodic basis.

17. The computer program product of claim 13, wherein the program instructions executable by the device cause the device to further perform:
receiving in a server coupled to the fixed storage a request to retrieve affirmative consent information pertaining to an event specified to have occurred in connection with a particular time of year;
retrieving from the fixed storage a set of all triple encrypted packages stored within a threshold period of time from the particular time of year;
decrypting each of the triple encrypted packages using a decryption key associated with the remote storage;
attempting brute-force decryption to the set using private keys for each of the requesting individual and the different individual; and,
storing in memory of the server two unencrypted sets of data resulting from the brute-force decryption, the two unencrypted sets reflecting the affirmative consent in response to the request.

* * * * *